(12) United States Patent
Buxbaum

(10) Patent No.: US 9,881,766 B2
(45) Date of Patent: *Jan. 30, 2018

(54) DIFFERENTIAL IMAGING WITH PATTERN RECOGNITION FOR PROCESS AUTOMATION OF CROSS SECTIONING APPLICATIONS

(71) Applicant: FEI Company, Hillsboro, OR (US)

(72) Inventor: Alexander Buxbaum, Portland, OR (US)

(73) Assignee: FEI Company, Hillsboro, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/082,848

(22) Filed: Mar. 28, 2016

(65) Prior Publication Data

US 2016/0211113 A1    Jul. 21, 2016

Related U.S. Application Data

(63) Continuation of application No. 14/526,971, filed on Oct. 29, 2014, now Pat. No. 9,297,727.

(Continued)

(51) Int. Cl.
*H01J 37/22* (2006.01)
*H01J 37/26* (2006.01)
(Continued)

(52) U.S. Cl.
CPC ............ *H01J 37/222* (2013.01); *G01N 1/286* (2013.01); *G01N 1/32* (2013.01); *G01N 1/44* (2013.01);
(Continued)

(58) Field of Classification Search
None
See application file for complete search history.

(56) References Cited

U.S. PATENT DOCUMENTS 5,436,449 A    7/1995    Takahashi et al.
7,388,218 B2   6/2008    Carleson
(Continued)

FOREIGN PATENT DOCUMENTS

CN    102207472 A    10/2011
EA       1812946 A1     8/2007
(Continued)

OTHER PUBLICATIONS

Kolb, U., et al., "Towards automated diffraction tomography: Part I—Data acquisition", Ultramicroscopy, 2007, pp. 507-513, vol. 107.

(Continued)

*Primary Examiner* — Michael Logie
(74) *Attorney, Agent, or Firm* — Scheinberg & Associates, PC; John B. Kelly

(57) ABSTRACT

A method for using differential imaging for applications involving TEM samples by allowing operators to take multiple images during a procedure involving a focused ion beam procedure and overlaying the multiple images to create a differential image that clearly shows the differences between milling steps. The methods also involve generating real-time images of the area being milled and using the overlays of the differential images to show small changes in each image, and thus highlight the ion beam milling location. The methods also involve automating the process of creating differential images and using them to automatically mill subsequent slices.

14 Claims, 13 Drawing Sheets

Related U.S. Application Data

(60) Provisional application No. 61/897,052, filed on Oct. 29, 2013.

(51) Int. Cl.

| | | |
|---|---|---|
| *G01N 1/28* | (2006.01) | |
| *H01J 37/304* | (2006.01) | |
| *H01J 37/305* | (2006.01) | |
| *G01N 1/32* | (2006.01) | |
| *G01N 1/44* | (2006.01) | |

(52) U.S. Cl.
CPC .......... *H01J 37/261* (2013.01); *H01J 37/304* (2013.01); *H01J 37/3056* (2013.01); *H01J 2237/08* (2013.01); *H01J 2237/20* (2013.01); *H01J 2237/221* (2013.01); *H01J 2237/226* (2013.01); *H01J 2237/262* (2013.01); *H01J 2237/30466* (2013.01); *H01J 2237/31745* (2013.01)

(56) References Cited

U.S. PATENT DOCUMENTS

| | | | |
|---|---|---|---|
| 7,897,918 B2 | 3/2011 | Phaneuf et al. | |
| 8,170,832 B2 | 5/2012 | Young et al. | |
| 8,399,831 B2 | 3/2013 | Faber et al. | |
| 9,297,727 B2* | 3/2016 | Buxbaum ................ | G01N 1/32 |
| 2004/0144924 A1 | 7/2004 | Asselbergs et al. | |
| 2008/0073580 A1* | 3/2008 | Phaneuf .............. | H01J 37/3005 |
| | | | 250/492.21 |
| 2008/0088831 A1* | 4/2008 | Mulders ................... | G01N 1/30 |
| | | | 356/237.2 |
| 2009/0135240 A1* | 5/2009 | Phaneuf ................. | G01N 1/286 |
| | | | 347/246 |
| 2010/0116977 A1 | 5/2010 | Young et al. | |
| 2011/0240852 A1* | 10/2011 | Tanner ................... | G01N 1/286 |
| | | | 250/307 |
| 2013/0248708 A1* | 9/2013 | Man ................... | G01N 23/2202 |
| | | | 250/307 |
| 2014/0061032 A1* | 3/2014 | Miller ...................... | G01N 1/32 |
| | | | 204/192.33 |
| 2014/0092230 A1* | 4/2014 | Langer ............... | G01N 23/2251 |
| | | | 348/80 |

FOREIGN PATENT DOCUMENTS

| | | |
|---|---|---|
| EP | 2149897 A1 | 2/2010 |
| WO | 2014014446 A1 | 1/2014 |

OTHER PUBLICATIONS

Ma, Yunpeng, "The mathematic magic of Photoshop blend modes for image processing", Multimedia Technology, 2011 International Conference on, IEEE, 2011, pp. 5159-5161.

Sardo, A., et al., "Digital beam control for 1-9 fast differential voltage contract", Scanning, 1984, pp. 125-126, vol. 6, No. 3.

Thomas, Robert, "Photoshop Blend Modes Explained—Photo Blog Stop", 2011, pp. 1-44, http://photoblogstop.com/photoshop/photoshop-blend-moes-explained.

Van Leer, B., et al., "Static vs. Dynamic FIB/SEM Methods for 3D Modeling", Microscopy and Microanalysis, 2007, pp. 1506-1507, vol. 13, No. S02.

* cited by examiner

DIFFERENTIAL IMAGING WITH PATTERN RECOGNITION FOR PROCESS AUTOMATION OF CROSS SECTIONING APPLICATIONS

This application is a continuation of U.S. patent application Ser. No. 14/526,971, filed on Oct. 29, 2014. This application claims priority to U.S. Prov. Application 61/897,052 filed Oct. 29, 2013 which is hereby incorporated by reference.

TECHNICAL FIELD OF THE INVENTION

The present invention relates to charged particle beam systems, such as focused ion beam systems.

BACKGROUND OF THE INVENTION

Transmission electron microscopes (TEMs) allow observers to see extremely small features, on the order of nanometers. In contrast to scanning electron microscopes (SEMs), which only image the surface of a material, TEMs also allow analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite side. Samples, also referred to as lamellae, are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface. The term "TEM" as used herein refers to a TEM or a STEM and references to preparing a sample for a TEM are to be understood to also include preparing a sample for viewing on a STEM. The term "S/TEM" as used herein also refers to both TEM and STEM.

Focused Ion Beam (FIB) microscope systems produce a narrow, focused beam of charged particles, and scan this beam across a specimen in a raster fashion, similar to a cathode ray tube. Unlike the SEM, whose charged particles are negatively charged electrons, FIB systems use charged atoms, hereinafter referred to as ions, to produce their beams. These ions are, in general, positively charged.

Removing material from a substrate to form microscopic or nanoscopic structures is referred to as micromachining, milling, or etching. When an ion beam is directed onto a semiconductor sample, it will eject secondary electrons, secondary ions (i+ or i−), and neutral molecules and atoms from the exposed surface of the sample. By moving the beam across the sample and controlling various beam parameters such as beam current, spot size, pixel spacing, and dwell time, the FIB can be operated as an "atomic scale milling machine," for selectively removing materials wherever the beam is placed. The dose, or amount of ions striking the sample surface, is generally a function of the beam current, duration of scan, and the area scanned. The ejected particles can be sensed by detectors, and then by correlating this sensed data with the known beam position as the incident beam interacts with the sample, an image can be produced and displayed for the operator. Determining when to stop processing is referred to as "endpointing." While there are several known methods for detecting when a micromachining process cuts through a first material to expose a second material, it is typical to stop laser processing before a change in material is reached, and so determining the end point is more difficult.

FIB systems are used to perform microsurgery operations for executing design verification or to troubleshoot failed designs. This usually involves "cutting" metal lines or selectively depositing metallic lines for shorting conductors together. FIB "rapid prototyping" is frequently referred to as "FIB device modification", "circuit editing" or "microsurgery." Due to its speed and usefulness, FIB microsurgery has become crucial to achieving the rapid time-to-market targets required in the competitive semiconductor industry.

Successful use of this tool relies on the precise control of the milling process. Current integrated circuits have multiple alternating layers of conducting material and insulating dielectrics, with many layers containing patterned areas. The milling rate and effects of ion beam milling can vary vastly across the device. This is the reason why endpointing is difficult to perform without it being destructive. Endpointing is generally done based on operator assessment of image or graphical information displayed on a user interface display of the FIB system. In most device modification operations, it is preferable to halt the milling process as soon as a particular layer is exposed. Imprecise endpointing can lead to erroneous analysis of the modified device.

As semiconductor device features continue to decrease in size from sub-micron to below 100 nm, it has become necessary to mill smaller and higher aspect ratios with ion beam currents. FIB operators rely on conventional methods using real-time images of the area being milled and a graphical data plot in real time, to determine proper endpoint detection. Generally, the FIB operator is visually looking for changes in brightness of the milled area to qualitatively determine endpoint detection. Such changes may indicate a transition of the mill through different materials, such as a metal/oxide interface. The operator uses the progression slice to slice and looks for changes that ultimately tell the operator where the milling is taking place, the changes in the sample, and the progression towards endpointing.

Modern techniques sometimes involve the use of dual beam systems, such as an a FIB and SEM combination systems that allow the user to slice through samples and create images of the sections "live," such as SPI—(simultaneous patterning and imaging mode), for real-time imaging feedback on the milling processes. TEM sample prep endpointing is a decision made in real time and it can be used in cross section patterns, but the sample is generally sliced in a manner that is also destructive. In addition, SPI images often create lower resolution due to the frame averaging of the images and the high image e-beam currents. The I-SPI is a system that allows images to update between various slices. These images are refreshed at every slice, but because consecutive slices involve only slight changes between images, the user often finds these image slices very difficult to follow.

There are generally two different ways to collect a stack of 2D SEM images of FIB milled surfaces for subsequent 3D modeling of volumes using a dual platform FIB/SEM instrument, i.e., in static or dynamic mode. In dynamic SEM imaging of FIB milled surfaces (i.e., SPI mode), SEM images are acquired in real time during the FIB milling process. In static image acquisition mode, the FIB is used to slice away material and then either paused or stopped so that a slow scan high resolution SEM image may be acquired.

This type of image acquisition can be easily programmed into an automated Slice and View algorithm or an intermittent or I-SPI mode of instrument operation.

In SPI mode, secondary electrons (SEs) are emitted and detected due to ion/solid interactions as well as electron/solid interactions. To swamp out the SE signal from the FIB milling in the SEM image, the SEM image acquisition must be performed by changing three critical SEM imaging parameters: (i) the SEM beam current must operate at approximately a factor of 2 or greater than the ion beam milling current, (ii) the SEM images must be acquired at very fast scan rates, and (iii) the SEM images must be acquired using frame averaging (e.g., as many as 32 or 64 frames may be required for large beam current milling). Thus, SE SEM acquisition of images obtained in SPI mode must be collected in a mode which is typically not used for highest resolution imaging. Alternatively, backscattered electron (BSE) SEM images can be collected in SPI mode where the SEs from the FIB milling produces negligible artifacts in the BSE imaging process. However, the timing of image acquisition during SPI mode is critical, and even the acquisition of BSE SEM images in SPI mode may be non-trivial.

SEM images acquired in SPI mode can obtain redundant and/or duplicate information from one or more slices. Thus, using SPI mode, one would have to manually search through the sequence of images to remove redundant images such that an accurate 3D model could be constructed. One could time each SE or BSE image saved such that it occurs only after a complete FIB slice, but this would require a prior knowledge of the material sputtering characteristics and would be difficult to exactly correlate the SEM acquisition time with the time needed to FIB through a slice. It is noted however that SPI mode is extremely useful for endpointing any FIB operation since FIB milling may be monitored in real time.

The advantage to the static Slice and View methods for 3D modeling is that a high resolution slow scan SEM image is acquired after each FIB milled slice is completed. Thus, each image corresponds uniquely to each FIB slice for easy volume determination. In addition, automated SEM beam shift and auto-focus corrections can be implemented to keep the region of interest centered and focused as sectioning progresses.

Prior art methods have tried to improve on FIB milling endpointing operations by generally creating a real-time ability to gauge the sensitivity to regions of interest on a sample site. For example, EP 1812946 A1, with a filing date of Nov. 15, 2005 (also published as U.S. Pat. No. 7,897,918), titled "System and method for focused ion beam data," (hereinafter as the '918 patent) discloses a system and method for improving FIB milling endpointing operations by using real-time graphical plots of pixel intensities with an increased sensitivity over native FIB system generated images and plots. This is done by receiving dwell point intensity values and creating raster pattern data to create areas of sensitivity. As shown in FIG. 9 of the '918 patent disclosed a method of using snapshot images taken progressively in a raster pattern. The frame generation is done using a CPB system. And as shown, the differential images 428, 430 are made using the individual slices.

This method has many shortcomings, which should be apparent. The accuracy and timelines of this procedure does not allow the operator full control of the endpointing nor would it allow the operator to see clear distinctions in patterns or defects. Further, the time consumption for this procedure would not allow the operator to perform this function in a manner that can enable real-time endpointing with concurrent use of progressive endpointing.

With current technologies that can be used to manipulate endpointing, there are generally two modes for collecting a series of SEM images of FIB-milled surfaces using a dual beam instrument: static mode and dynamic mode. In dynamic SEM imaging of FIB milled surfaces, SEM images are acquired in real time during the FIB milling process. In static image acquisition mode, the FIB is used to slice away material and then either paused or stopped so that a slow scan high resolution SEM image may be acquired.

One challenge during dynamic mode imaging, is to know exactly where the beam is hitting the sample, and what part of the sample is being milled at any given moment. Particularly in the preparation of a TEM sample, the user must determine in real time when to stop thinning a sample. Thinning the sample too much can destroy it. The lower resolution of dynamic mode can make it difficult to know how much the sample has been thinned.

Thus, the user typically watches the progression from slice to slice and looks for changes from slice to slice. This helps him know where the milling is taking place (where the beam "is hitting"), helps him see changes in his sample, and helps him follow progress towards the endpoint—where the user manually stops the mill, e.g., endpointing.

What is needed is a method of precisely and efficiently showing the operator changes in the slices so that real-time endpointing can be done in a better manner that produces less errors and higher productivity. The method lends itself further with other automated processes that increase throughput and reproducibility of TEM samples.

SUMMARY OF THE INVENTION

An object of the invention, therefore, is to provide an improved method for endpointing that allows the operator to view the samples in a manner that can visually distinguish slices. Preferred embodiments of the present invention use overlays of differential images to further improve I-SPI modes and provide improved methods for endpointing samples that together increases throughput and reproducibility of TEM sample creation.

Another object of the invention is to provide an improved method for improved yield, speed, and accuracy when performing endpointing procedures. Preferred embodiments of the present invention use overlays of differential images to better distinguish differences between slices that improve the visual contract of endpointing results that lead to improved yield, speed, and accuracy. By using overlays, there is the potential to use successive overlays that will create a pipeline of images, which allows the operator to process the first set of images while the pipeline of successive images is being processed. This allows for faster throughput and higher efficiency.

Another object of the invention is to provide an endpointing procedure that can be automated. Preferred embodiments of the present invention allow systems to use overlays that automatically show differences in overlays of differential images.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Generally, the present invention provides methods for improving FIB milling endpointing operations. The methods involve generating real-time images of the area being milled and real-time images that can be overlayed to create differential images.

A preferred embodiment of the invention uses software that can create the differential images and a controller that can process and even act on the results of a differential image. The differential images are capable of detecting milling that is not occurring uniformly across a sample. The differential images may be used in a manual process in that the user can use the detected milling patterns of the differential image to correct in subsequent milling.

In another preferred embodiment, the user can use the differential images in an automated process. For example, using conventional automated tilting and rotating features, a controller can be programmed to recognize the milling patterns and identify instances where the milling patterns are not uniform. In the automated process, the controller can adjust the tilt and rotation of the sample stage or the workpiece in some manner to correct for the non-uniformity.

Figure 8:
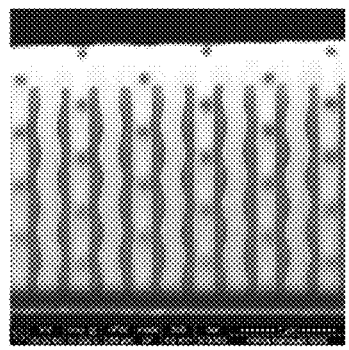
FIG. 8 is a micrograph image showing a sample before a milling operation.
Figure 9:
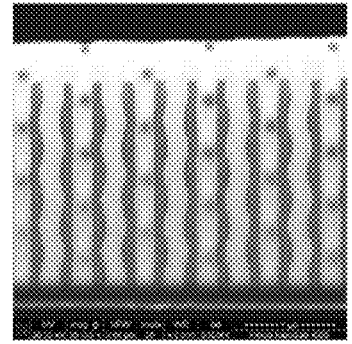
FIG. 9 is a micrograph image showing the sample after a milling operation.
Figure 10:
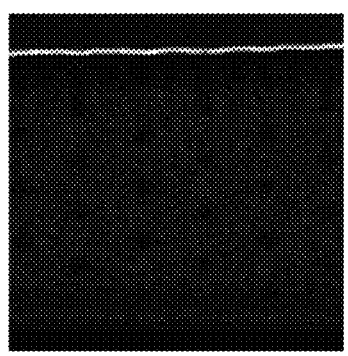
FIG. 10 is an image formed by subtracting the image of FIG. 8 from the image of FIG. 9.
Figure 11:
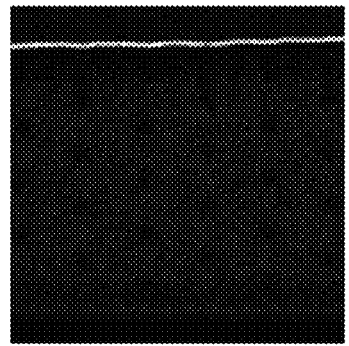
FIG. 11 is an image formed by subtracting the image of FIG. 9 from the image of FIG. 8.
Figure 12:
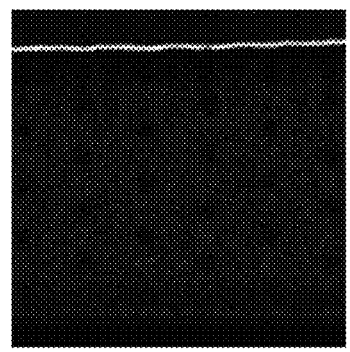
FIG. 12 is an image formed by blending the image of FIG. 10 with the image of FIG. 11.

A differential image is the result of subtraction operations between two images. For example, in FIG. 8 and FIG. 9, the corresponding gray level information in each pixel of two images can be subtracted out, which would result in a differential image for each pixel. Although these images appear very similar, FIG. 9 was collected after a significant amount of milling, using a cleaning cross section. A cleaning cross section is a type of milling pattern (e.g., milling in a line by line progression rather than a box area). A dual beam system operator finds it very difficult to determine what has changed. The resulting differential images are shown in FIG. 10 and FIG. 11. FIG. 10 is the result of subtracting FIG. 8 from FIG. 9, and FIG. 11 is a result of subtracting FIG. 9 from FIG. 8. Finally, the two results (FIG. 10 and FIG. 11) can be blended (e.g., "lighten" blend mode in Photoshop) in FIG. 12, to show overall what has changed the most in the sample.

These calculations can be applied in almost real time to show a nearly live version of differential images on a user interface. This would provide the operator nearly real time feedback on what is milling in his sample and would enable higher quality sample preparation, which would far improve any available technologies to use such high resolution real-time data. The differential image may be displayed by itself or overlayed onto a conventional image to show what has changed between milling passes of the FIB. The differential image could be displayed as a flashing overlay on the last slice. In other embodiments, these highlights where the ion beam is milling, that is, where it is hitting the sample.

In accordance with one embodiment of the current invention, a method for performing endpointing on a sample is disclosed. To perform the procedure that includes imaging the sample, the sample is placed in a system with both a charged particle beam system, such as a focused ion beam, and an electron beam system. After the sample is loaded in the system, the electron beam system is used to create an image on a first surface. For purposes of the current invention, the surface to be imaged is a cross sectional slice of the sample. The charged particle beam is used to slice through the sample and create a new sample surface, or a second surface of the sample. Once again, the electron beam is used to image the sample on the second surface of the sample, which again is used to create a second cross sectional view of the sample.

Figure 1:
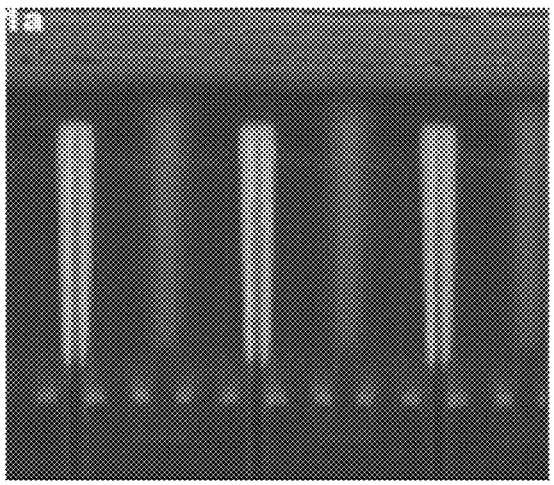
FIG. 1 is a diagram of side by side images of TEM sample slices using conventional methods.
Figure 1:
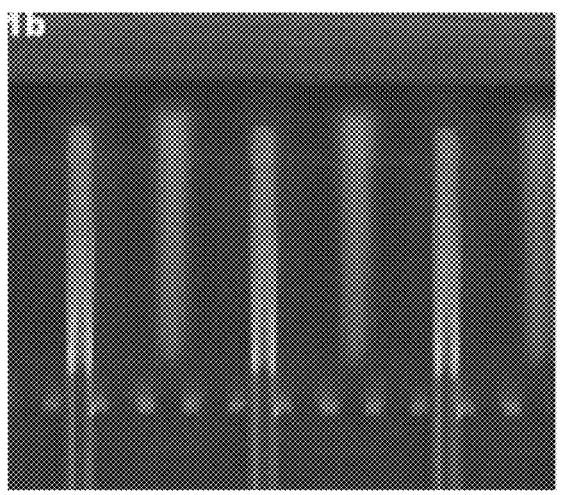
Figure 1:
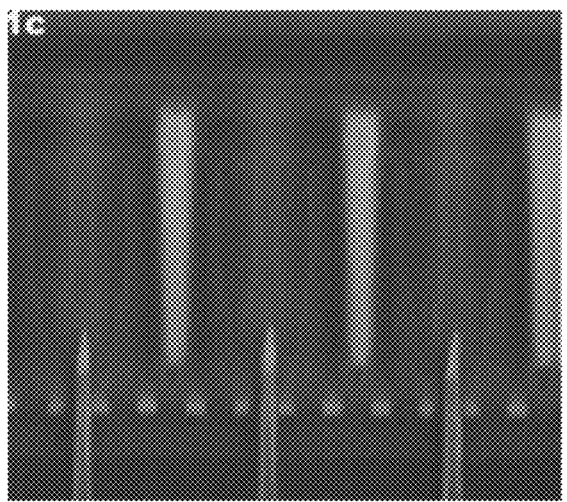

FIG. 1 is a figure of diagram of side by side images of SEM images acquired during SPI mode spanning more than 20 individually saved images. Using conventional methods, an operator would have to view these individual slices manually by eye to determine minute differences in each slice to determine the progression of differences in each slice. Once the differences are determined, the operator than can use the difference to determine the proper region of interest and proceed with the next milling step. For example, the operator can use the difference to determine which part of his sample is currently being milled. This helps the operator make adjustments to the milling process. This can be performed by scan rotation, beam shift, or the advancement of the line milling of a cleaning cross section.

Alternatively, the operator can use the differences in each progressive slice to follow the progression of milling on the sample. This allows the operator to anticipate where sample material is going to be milled next. Understanding where the material sample will be milled next helps in the preparation for endpointing. It should be understood that in another preferred embodiment, the automation of this process is contemplated. If the differences in the milling progressive slices can be automatically identified, then a controller (not shown) can be programmed to make the adjustments in scan rotation, beam shift, or advancement of the line milling of a cleaning cross-section based on the identified patterns. Thus, the differential image can be used to identify the milling patterns, which then allows for the controller to make those adjustments. Adjustments can be automated in the milling process, as well, such as making tilting and rotation adjustments on the sample stage or workpiece (not shown). Conventional controllers and conventional means are known in the art to allow for the automated controls of the sample stage, workpiece, or beam changes.

In accordance with another embodiment of the current invention, software is used to create a digital version of the image of the first surface and the second surface, and software is additionally used to overlay the images and create a differential image. The images are compared with each other and the resultant third image shows the difference made from the charged particle beam to create the second surface.

Figure 2:
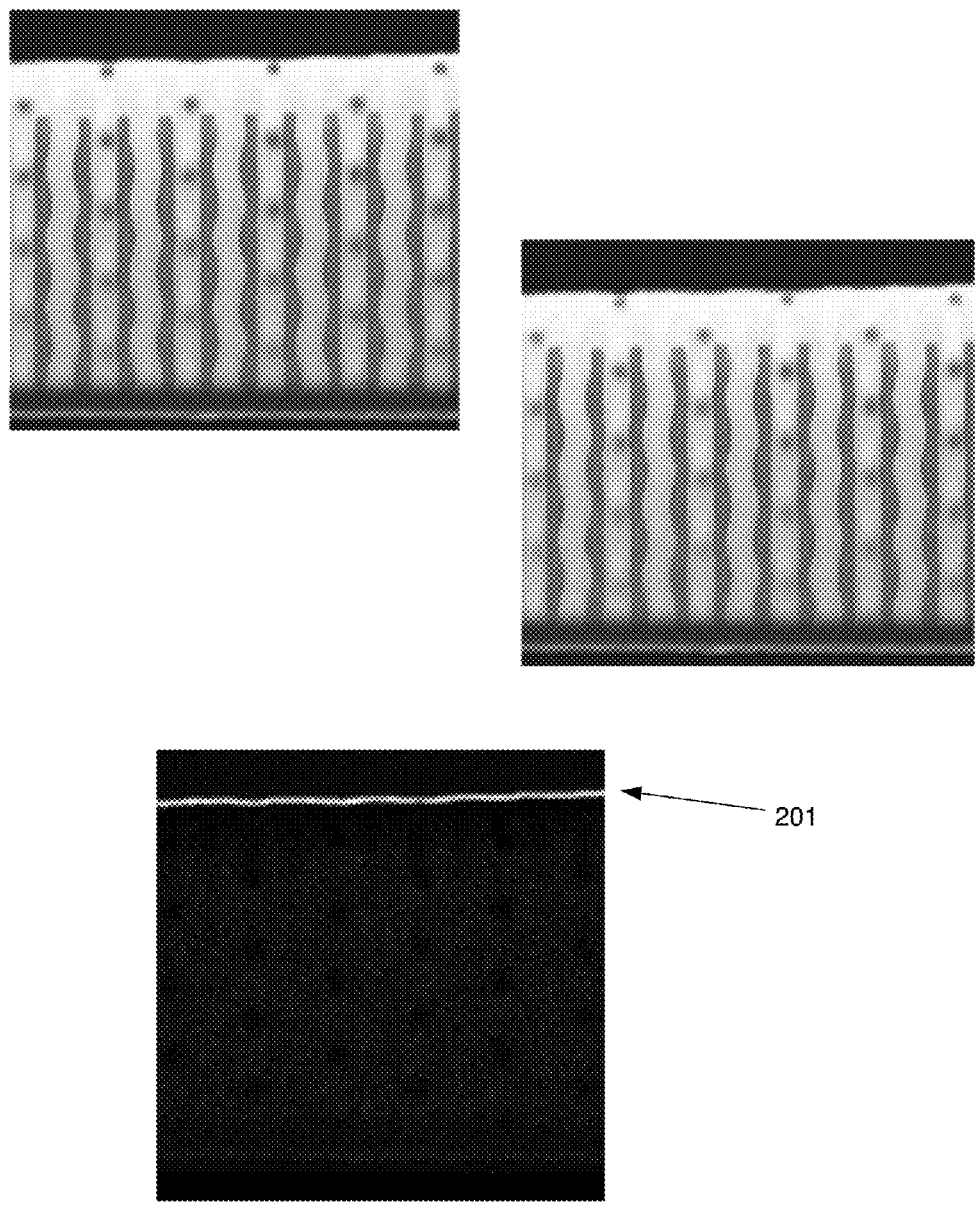
FIG. 2 shows a diagram showing TEM sample preparations according to the current invention wherein the diagram represents slices of TEM samples that are overlayed.

FIG. 2 shows a conventional method of using differential images for TEM samples wherein the first two samples show progressive slices of a TEM sample and where the third image shows the differential image showing the differential line 201. As shown, the operator can view the differential image and identify the progressive nature of each slice. The line 201 can also be identified by a controller in an automated process using conventional methods, such as reading digital pixels from a scanned image (process not shown).

The method in accordance with the current invention uses the software to determine color or shade information in each pixel of the images. Various software is capable of comparing images at a pixelated level. Photoshop has a Blend Mode wherein pixels are compared between the first image and the second image. The software allows wherein the pixels that are darker in one image is replaced with pixels that are lighter in the making of the third image. In this mode, pixels from one image that are the same in color or shade as the pixels in the second image are left alone in the third image. This creates a differential image that highlights the differences in milling patterns made by the milling process.

Figure 3A:
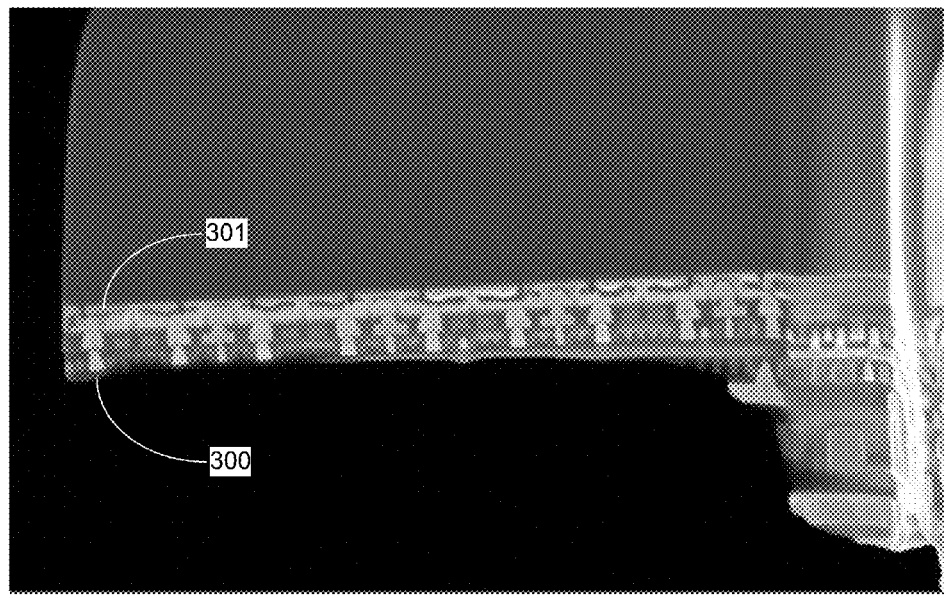
FIG. 3A is a sample TEM slice labeled "n"
Figure 3B:
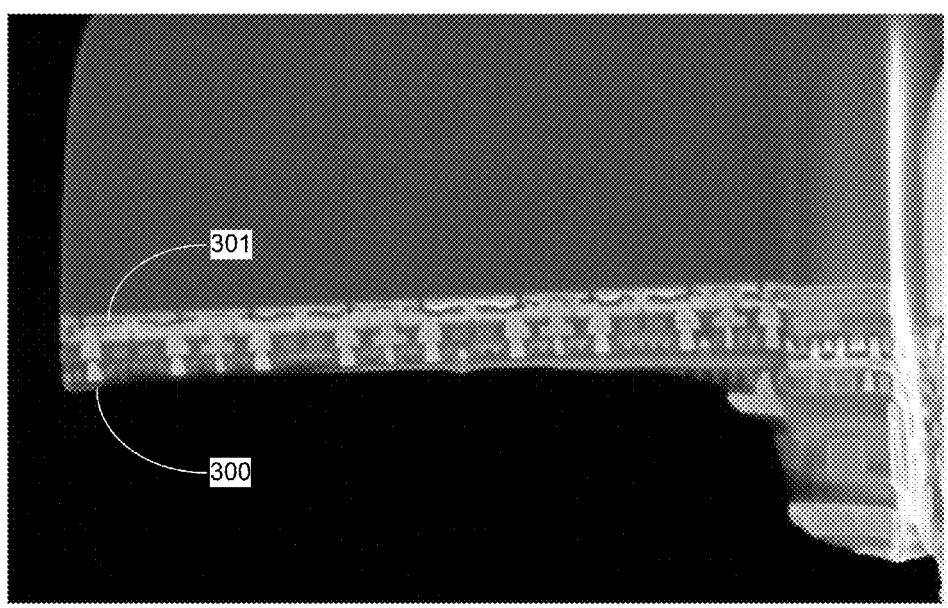
FIG. 3B is the next sample TEM slice labeled "n+1"
Figure 3C:
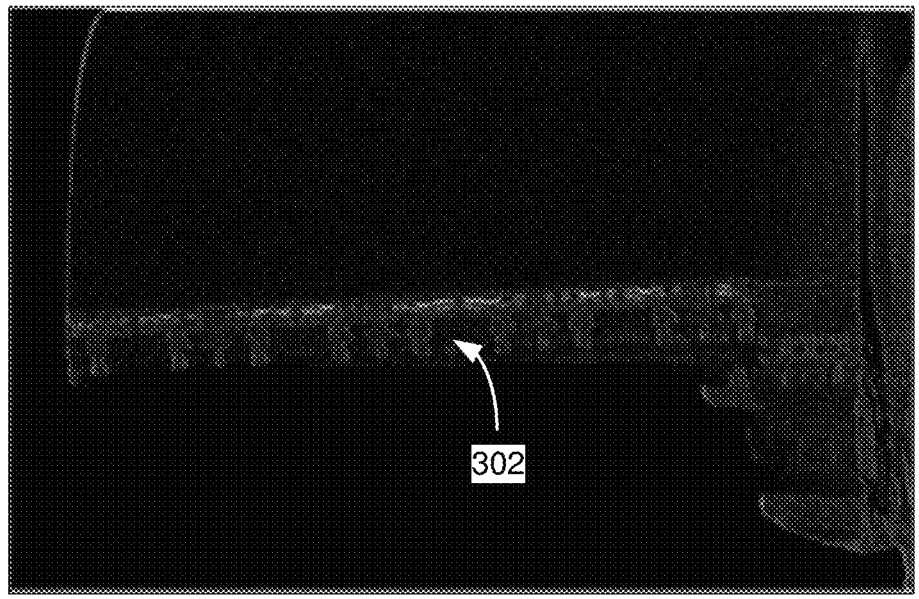
FIG. 3C is the differential image of FIGS. 3A and 3B.

FIG. 3A is a sample TEM slice labeled "n" and FIG. 3B is the next sample TEM slice labeled "n+1". The sample 300 has milling sites 301 that are very difficult to distinguish with the human eye. Similar to the description above, once the image is overlayed and a differential image is created, the differences in milling is highlighted by image shown in FIG. 3C.

Figure 3D:
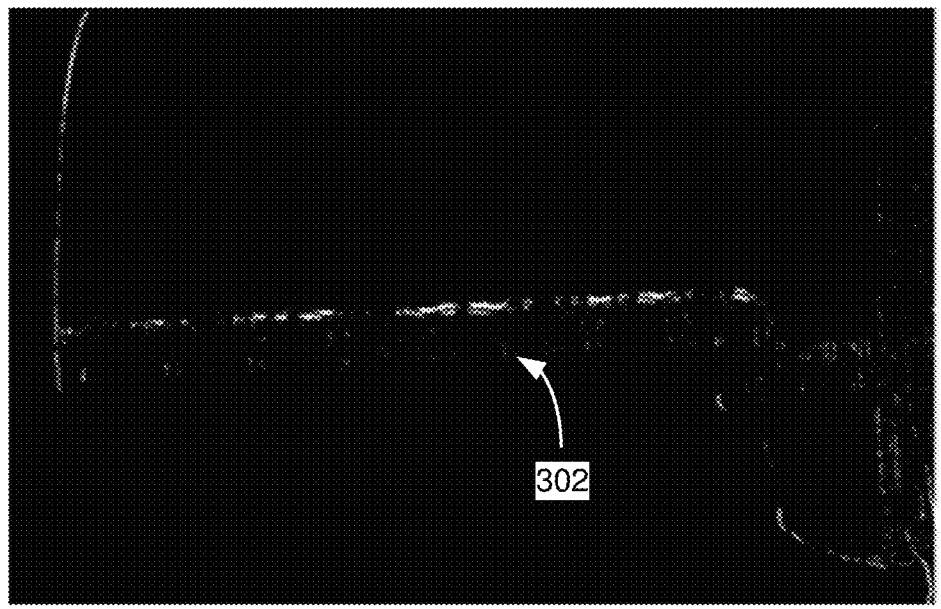
FIG. 3D is the differential image of FIGS. 3A and 3B that is processed.

FIG. 3D is the resultant image of the differential after the subtraction is made using the software. As shown, the highlighted differences in 302 is much easier to identify with the differential overlayed image.

Much like as shown above, the differential image can be displayed over the last image periodically in a flashing overlay that creates highlights wherein the ion beam last milled. This can also be used by a controller to determine the dwell point of the next subsequent milling process if one is needed.

Figure 4A:
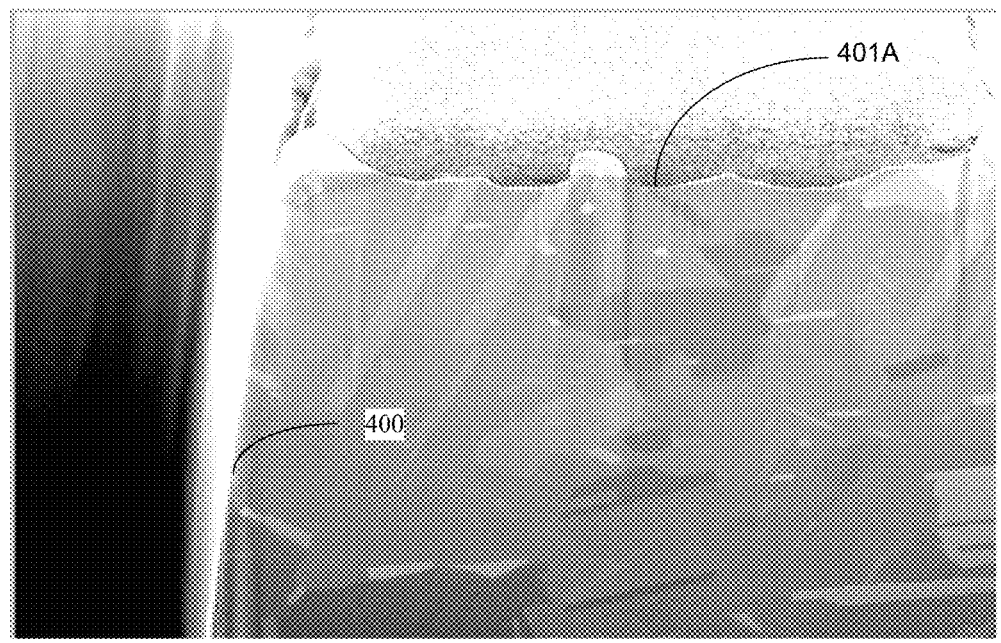
FIG. 4A is a cross sectional image of a copper grain TEM sample.
Figure 4B:
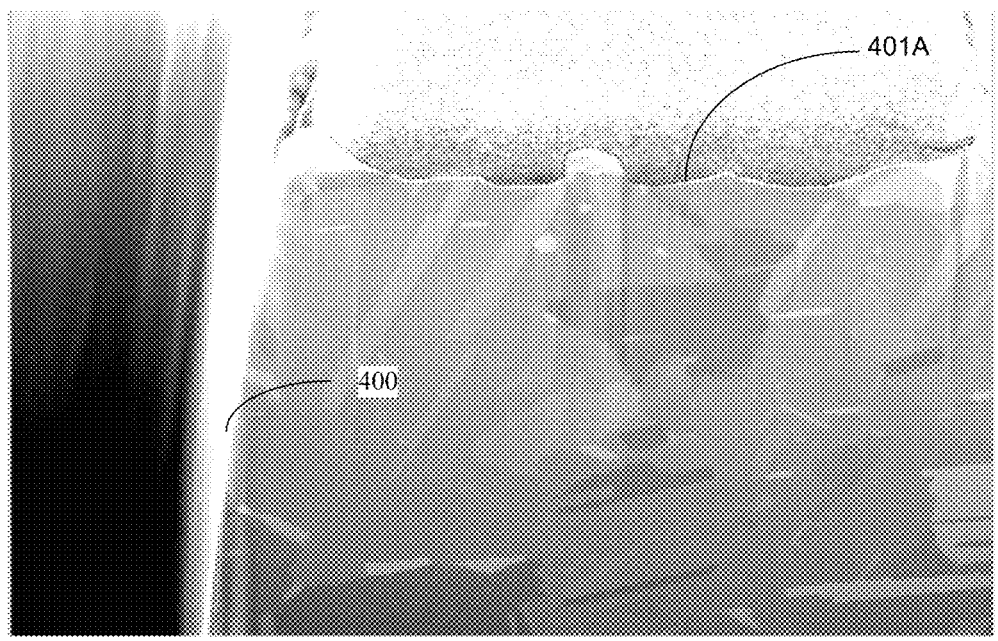
FIG. 4B is another cross sectional image of a copper grain TEM sample in the series.

FIGS. 4A and 4B are cross sectional images 400 of a copper grain TEM sample. Again, in the conventional method, the operator would normally have to determine minute differences in these sample surfaces 401A to determine the next or subsequent milling process.

Figure 4C:
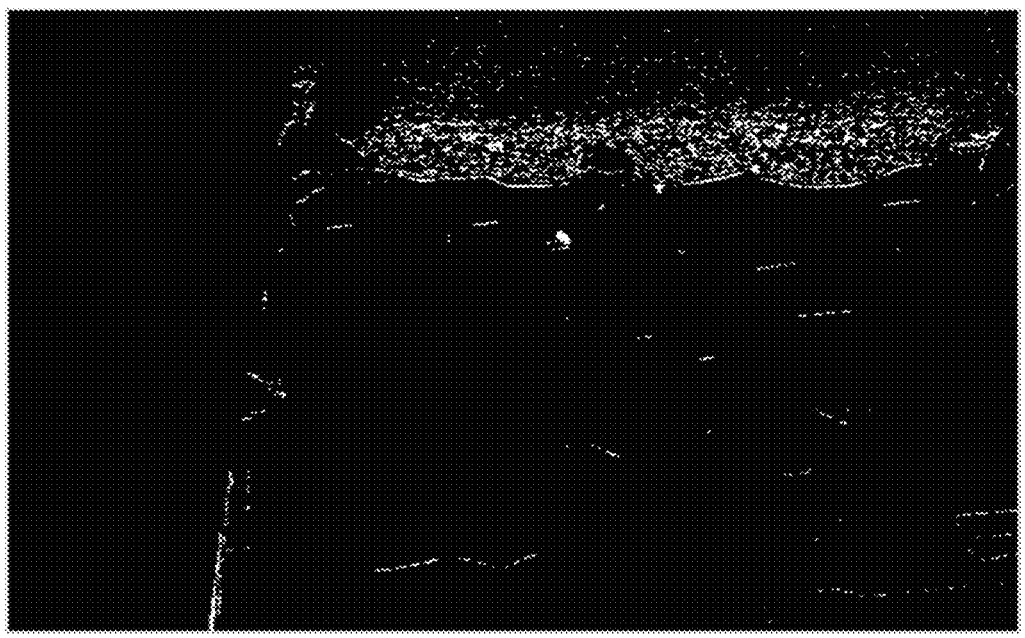
FIG. 4C is the differential of the cross sectional images of copper grain TEM samples.

FIG. 4C is the differential of the cross sectional images of copper grain TEM samples that again show highlights in the differences made by the milling processes of the current invention. The method in accordance with the current invention is used to create many slices or surfaces of the sample site using the charged particle beam. Subsequent differential images can be created by using the same method and same software to compare subsequent slices of images.

As described above, a controller can be used to automate the image collection of the SEM images and the creation of the differential image. The controller may be used to determine the subsequent dwell points and automatically mill the subsequent regions of interest on the surfaces using the highlighted differences from the differential image. The methods used in these procedures are performed in real time feedback so that an operator can mill a sample with the FIB immediately following the creation of the differential image.

In another embodiment of the current invention, the differential image of a target structure and its associated acquired image can be defined by the image of low contrast differences in the images. Thus, this is a different application than ones that allow the operator to use milling progressions with a differential image from one slice to the next. In another application, the operator can clear a particular layer using FIB milling (e.g., ILD in an IC circuit) and stop the milling process when the next layer is exposed (e.g., SiN or metal layer). The automated system or manual operator can monitor the differential image and detect a contrast change (above a threshold) in a particular part of the image (user definable region of interest). The automated feature, which requires significant manipulation at a microscopic level, reduces human error and expedites the whole milling process, which stops the milling process when a given threshold is met.

Figure 5A:
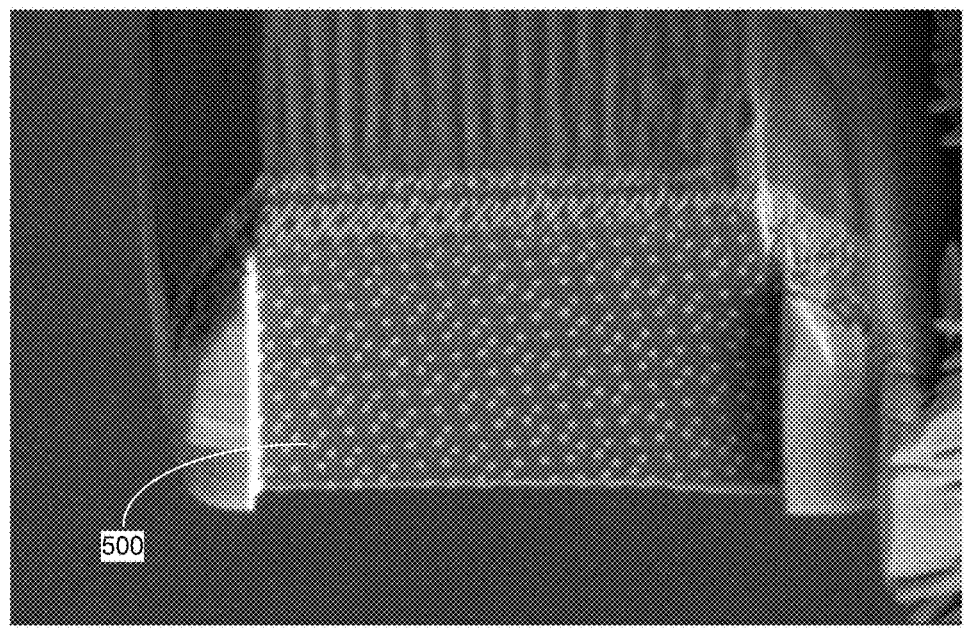
FIG. 5A is a TEM sample 22 nm plan view having slice n.
Figure 5B:
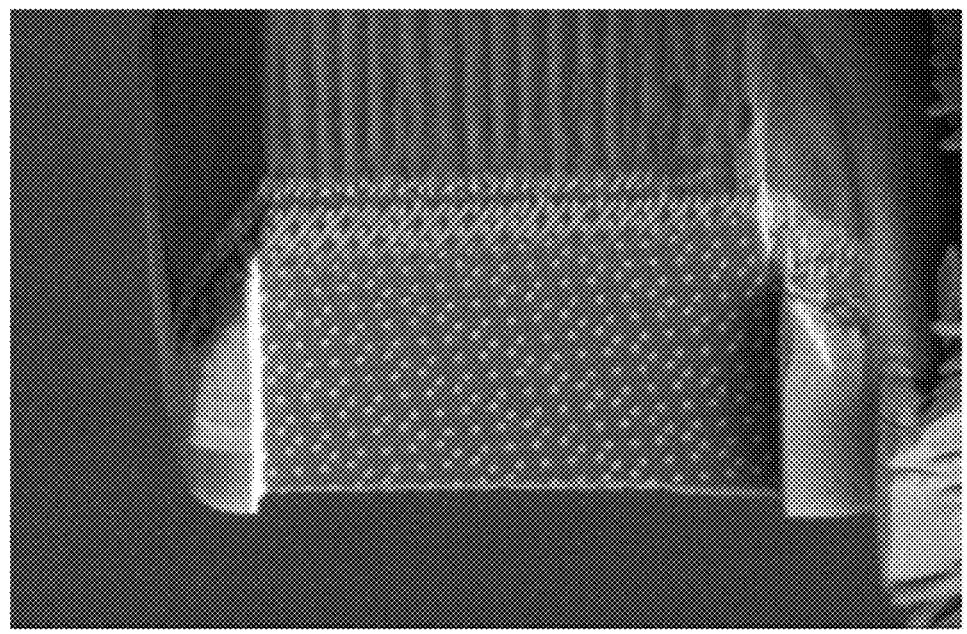
FIG. 5B is a TEM sample 22 nm plan view having slice n+1.
Figure 5C:
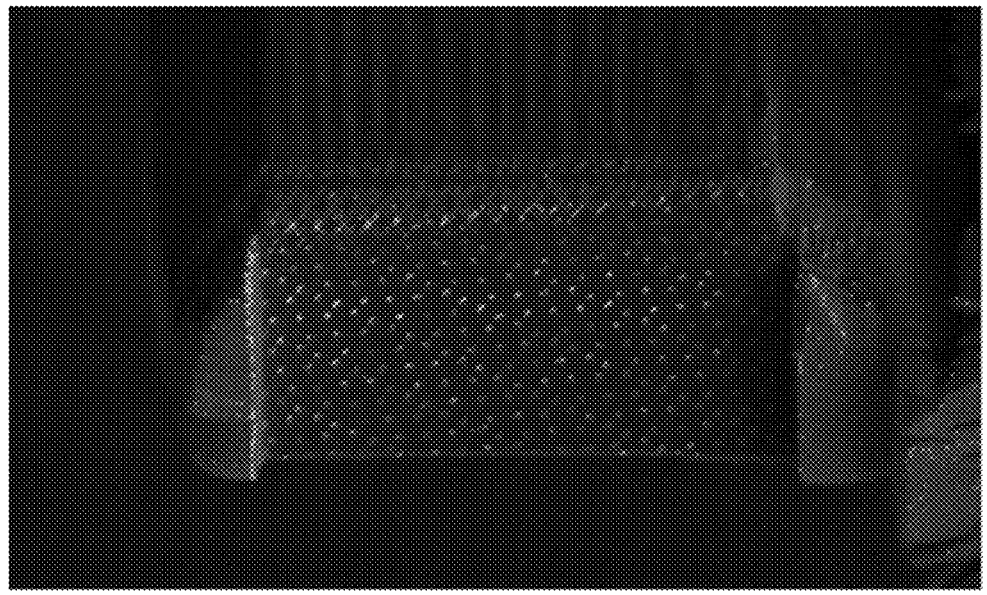
FIG. 5C is the overlay process view with slice n+1 of FIGS. 5A and 5B.
Figure 5D:
FIG. 5D is the overlayed differential view according to an embodiment of the current invention.
Figure 5E:
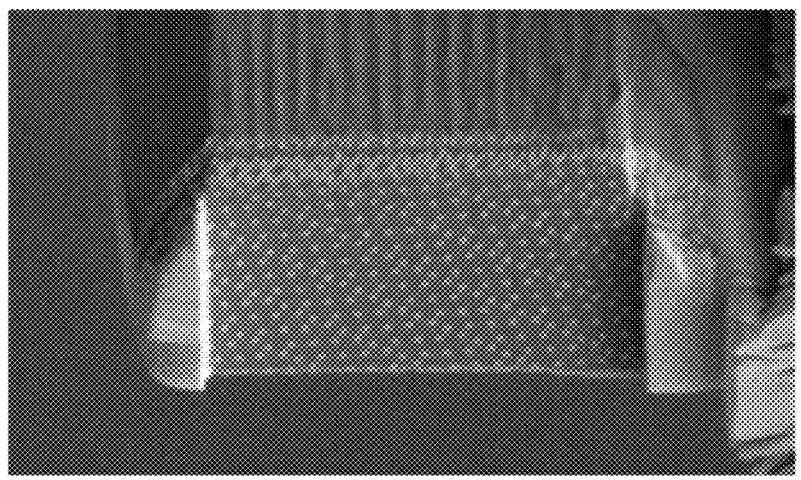
FIG. 5E is a TEM sample of a 22 nm plan view having the label slice n+2.
Figure 5F:
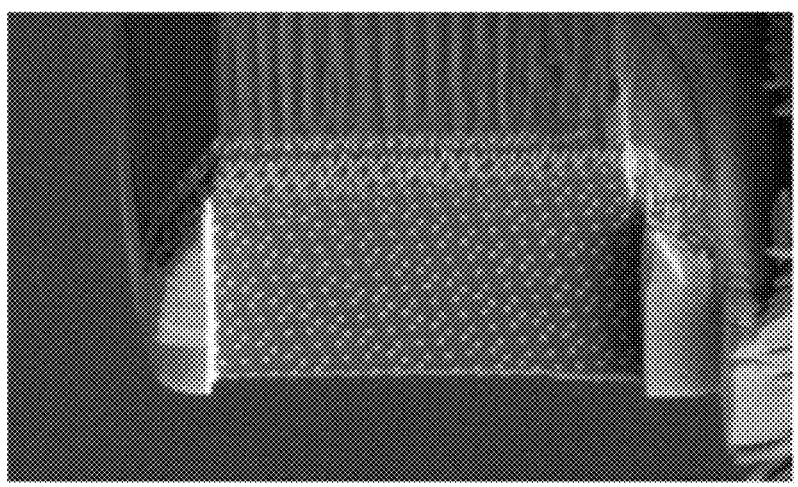
FIG. 5F is a TEM sample of a 22 nm plan view having the label slice n+3.
Figure 5G:
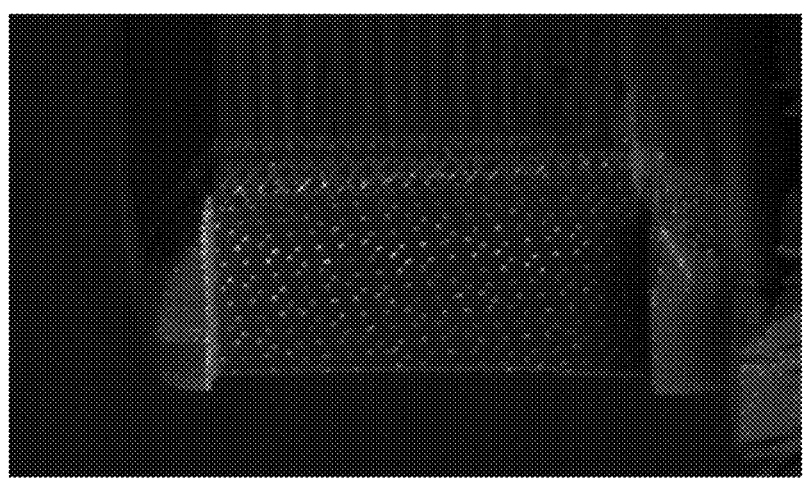
FIG. 5G is the overlayed differential view according to an embodiment of the current invention of FIGS. 5A-5F.
Figure 5H:
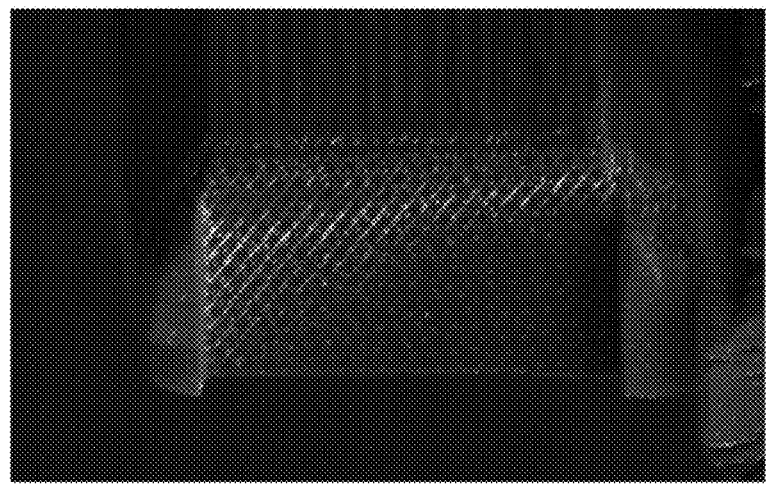
FIG. 5H is the overlayed image showing the slice n+3.
Figure 5I:
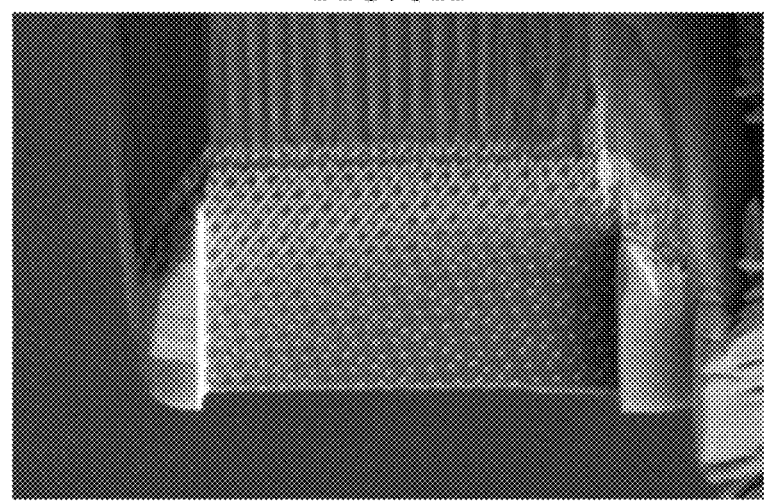
FIG. 5I is the differential image showing slice n+3.
Figure 5J:
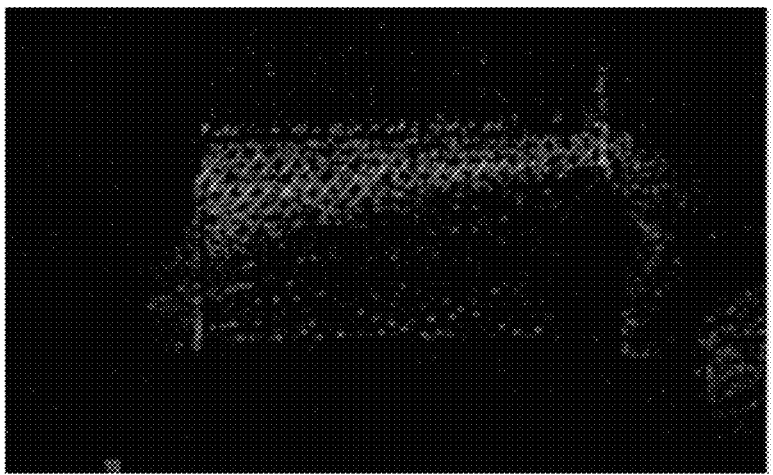
FIG. 5J is a flashing overlay showing slice n+3 in accordance with the current invention.

To show the extent of multiple slices of an SEM sample, FIG. 5A shows a TEM sample 500 22 nm plan view having slice "n." FIG. 5B is a TEM sample 22 nm plan view having slice "n+1." FIG. 5C is the overlay process view with FIGS. 5A and 5B. FIG. 5D is the overlayed differential view according to an embodiment of the current invention. Again, as shown, the differential image 505 creates easy locations for differences from the first two images. FIG. 5E is a TEM sample of a 22 nm plan view having the label slice "n+2." FIG. 5F is a TEM sample of a 22 nm plan view having the label slice "n+3." FIG. 5G is the overlayed differential view according to an embodiment of the current invention of FIGS. 5A-5F wherein the overlay is of a differential image ((n+1)−n) on top of an image (n+1). As shown the contrast allows the operator to clearly identify current milling activity of the milling process.

As shown in FIG. 5G, the methods can be reversed so that the first scan image is overlayed over the second scan image, which creates a negative reverse differential image. Subsequently, these differential images can be overlayed with each other or with other slices to highlight various differences.

Furthermore, the imaging of the scans are performed using simultaneous patterning and imaging, which allows the operator to use the FIB to slice away material in an automated slice and view algorithm while at the same time processing other slices. This allows for a continual processing of the slices that result in much higher throughput and efficiency.

Thus, in TEM sample preparation, this process can improve yield, speed, and accuracy. The process facilitates automatic endpointing through the use of pattern recognition on the differential image. A real image can also be compared to a calculated image using images derived from CAD data. The image processing can be performed while the next image is captured thereby speeding the throughput of processing the images. The process is useful in a variety of applications besides TEM sample preparation. The process can also be used in tomograph. For example, in viewing biological samples using cryo-tomograph, the system can learn from site A what to find at site B, and the system can cease milling after the region of interest is no longer visible.

Figure 6:
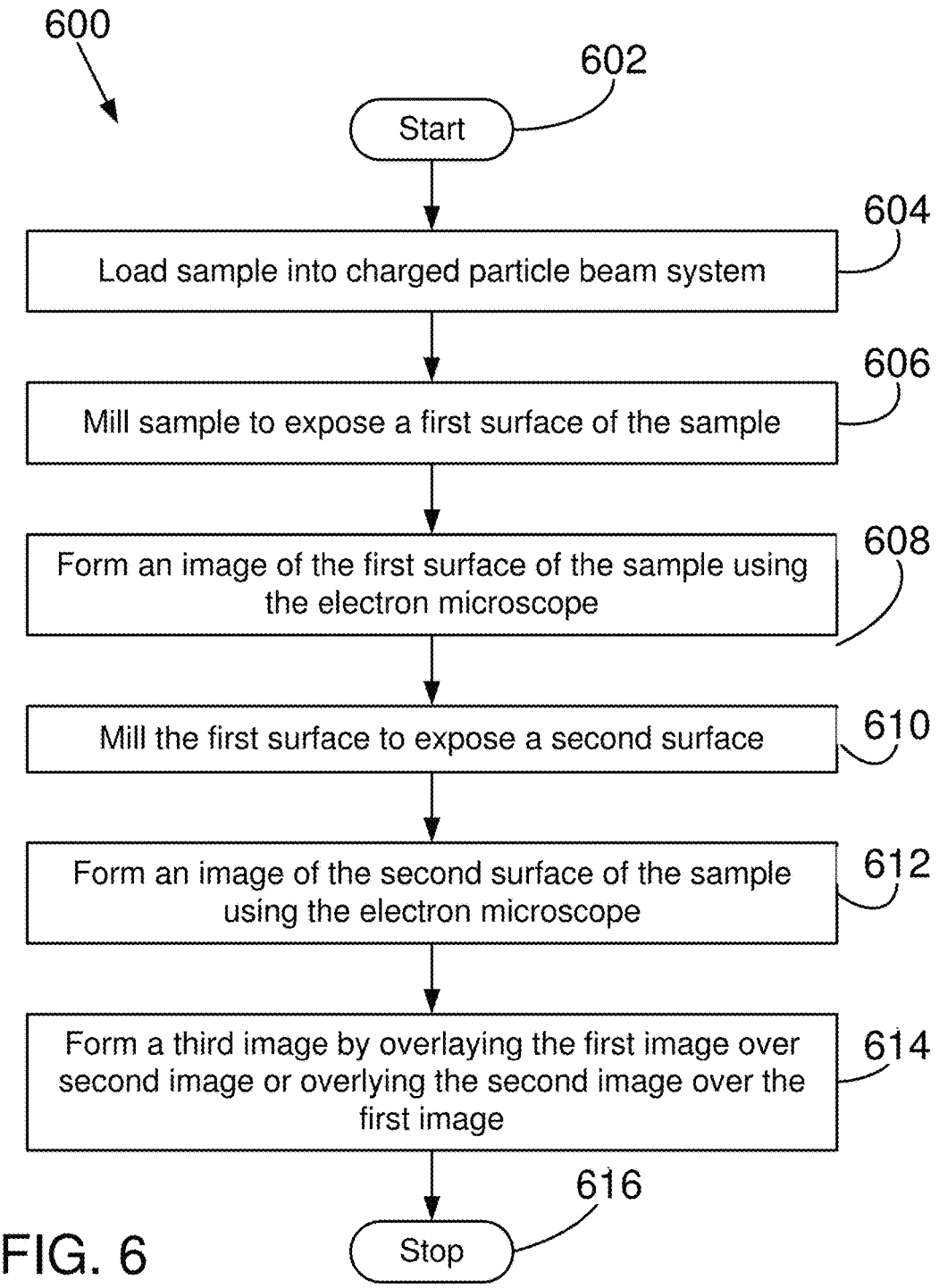
FIG. 6 is a flowchart 600 showing an exemplary method of using differential imaging to perform endpointing in a charged particle beam system in accordance with embodiments of the present invention.

FIG. 6 is a flowchart 600 showing an exemplary method of using differential imaging to perform endpointing in a charged particle beam system in accordance with embodiments of the present invention. The method begins at step 602 and proceeds to step 604. At step 604, the sample is loaded into the charged particle beam system. The charged particle beam system includes an ion beam and electron microscope. At step 606, the sample is milled, using the ion beam, to expose a first surface of the sample. At step 608, an image is formed, using the electron microscope, of the first surface of the sample. At step 610, the first surface of the sample is milled, using the ion beam, to expose a second surface of the sample. At step 612, a second image of the second surface of the sample is formed using the electron microscope. At step 614, a third image is formed by overlaying the second image over the first image. The third image is a differential image formed by subtracting the second image from the first image. The third image shows the difference made from the ion beam milling to create the second surface.

Figure 7:
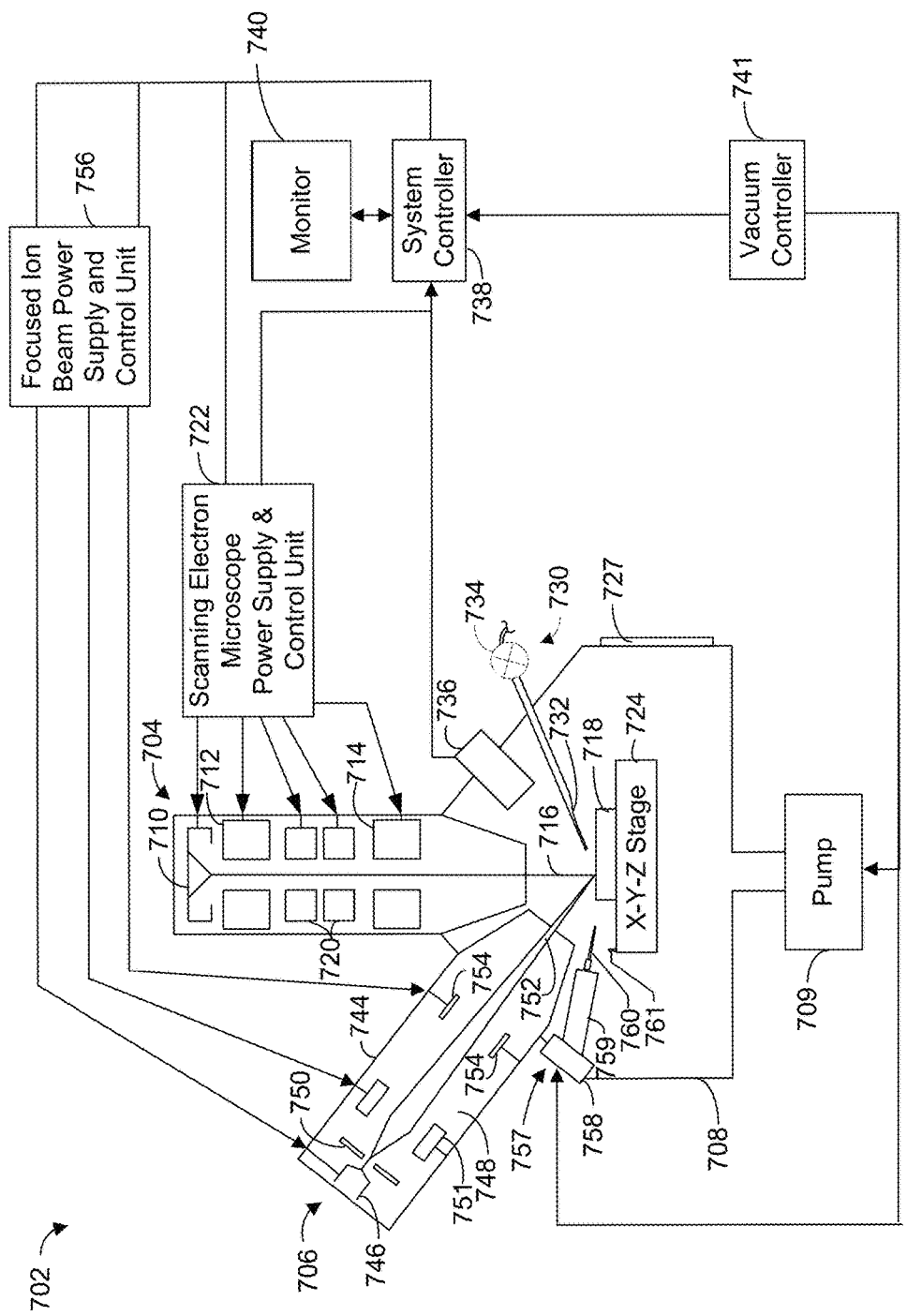
FIG. 7 depicts of an exemplary dual beam SEM/FIB system 702 that is equipped to form samples and move them to a TEM grid.

FIG. 7 depicts of an exemplary dual beam SEM/FIB system 702 that is equipped to form samples and move them to a TEM grid. Suitable dual beam systems are commercially available, for example, from FEI Company, Hillsboro, Oreg., the assignee of the present application. While an example of suitable hardware is provided below, the invention is not limited to being implemented in any particular type of hardware.

Dual beam system 702 has a vertically mounted electron beam column 704 and a focused ion beam (FIB) column 706 mounted at an angle of approximately 52 degrees from the vertical on an evacuable specimen chamber 708. The specimen chamber may be evacuated by pump system 709, which typically includes one or more, or a combination of, a turbo-molecular pump, oil diffusion pumps, ion getter pumps, scroll pumps, or other known pumping means.

The electron beam column 704 includes an electron source 710, such as a Schottky emitter or a cold field emitter, for producing electrons, and electron-optical lenses 712 and 714 forming a finely focused beam of electrons 716. Electron source 710 is typically maintained at an electrical potential of between 500 V and 30 kV above the electrical potential of a work piece 718, which is typically maintained at ground potential.

Thus, electrons impact the work piece 718 at landing energies of approximately 500 eV to 30 keV. A negative electrical potential can be applied to the work piece to reduce the landing energy of the electrons, which reduces the interaction volume of the electrons with the work piece surface, thereby reducing the size of the nucleation site. Work piece 718 may comprise, for example, a semiconductor device, microelectromechanical system (MEMS), data storage device, or a sample of material being analyzed for its material characteristics or composition. The impact point of the beam of electrons 716 can be positioned on and scanned over the surface of a work piece 718 by means of deflection coils 720. Operation of lenses 712 and 714 and deflection coils 720 is controlled by scanning electron microscope power supply and control unit 722. Lenses and deflection unit may use electric fields, magnetic fields, or a combination thereof.

Work piece 718 is on movable stage 724 within specimen chamber 708. Stage 724 can preferably move in a horizontal plane (X-axis and Y-axis) and vertically (Z-axis) and can tilt approximately sixty (60) degrees and rotate about the Z-axis. A door 727 can be opened for inserting work piece 718 onto X-Y-Z stage 724 and also for servicing an internal gas supply reservoir (not shown), if one is used. The door is interlocked so that it cannot be opened if specimen chamber 708 is evacuated.

Mounted on the vacuum chamber are one or more gas injection systems (GIS) 730. Each GIS may comprise a reservoir (not shown) for holding the precursor or activation materials and a needle 732 for directing the gas to the surface of the work piece. Each GIS further comprises means 734 for regulating the supply of precursor material to the work piece. In this example the regulating means are depicted as an adjustable valve, but the regulating means could also comprise, for example, a regulated heater for heating the precursor material to control its vapor pressure.

When the electrons in the electron beam 716 strike work piece 718, secondary electrons, backscattered electrons, and Auger electrons are emitted and can be detected to form an image or to determine information about the work piece. Secondary electrons, for example, are detected by secondary electron detector 736, such as an Everhart-Thornley detector, or a semiconductor detector device capable of detecting low energy electrons. Signals from the detector 736 are provided to a system controller 738. Said controller 738 also controls the deflector signals, lenses, electron source, GIS, stage and pump, and other items of the instrument. Monitor 740 is used to display user controls and an image of the work piece using the signal The chamber 708 is evacuated by pump system 709 under the control of vacuum controller 741. The vacuum system provides within chamber 708 a vacuum of approximately 7×10-6 mbar. When a suitable precursor or activator gas is introduced onto the sample surface, the chamber background pressure may rise, typically to about 5×10-5 mbar.

Focused ion beam column 706 comprises an upper neck portion 744 within which are located an ion source 746 and a focusing column 748 including extractor electrode 750 and an electrostatic optical system including an objective lens 751. Ion source 746 may comprise a liquid metal gallium ion source, a plasma ion source, a liquid metal alloy source, or any other type of ion source. The axis of focusing column 748 is tilted 52 degrees from the axis of the electron column. An ion beam 752 passes from ion source 746 through focusing column 748 and between electrostatic deflectors 754 toward work piece 718.

FIB power supply and control unit 756 provides an electrical potential at ion source 746. Ion source 746 is typically maintained at an electrical potential of between 1 kV and 60 kV above the electrical potential of the work piece, which is typically maintained at ground potential. Thus, ions impact the work piece at landing energies of approximately 1 keV to 60 keV. FIB power supply and control unit 756 is coupled to deflection plates 754 which can cause the ion beam to trace out a corresponding pattern on the upper surface of work piece 718. In some systems, the deflection plates are placed before the final lens, as is well known in the art. Beam blanking electrodes (not shown) within ion beam focusing column 748 cause ion beam 752 to impact onto blanking aperture (not shown) instead of work piece 718 when a FIB power supply and control unit 756 applies a blanking voltage to the blanking electrode.

The ion source 746 typically provides a beam of singly charged positive gallium ions that can be focused into a sub one-tenth micrometer wide beam at work piece 718 for modifying the work piece 718 by ion milling, enhanced etch, material deposition, or for imaging the work piece 718.

A micromanipulator 757, such as the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 757 may comprise precision electric motors 758 positioned outside the vacuum chamber to provide X, Y, Z, and theta control of a portion 759 positioned within the vacuum chamber. The micromanipulator 757 can be fitted with different end effectors for manipulating small objects. In the embodiments described herein, the end effector is a thin probe 760. A micromanipulator (or microprobe) can be used to transfer a TEM sample (which has been freed from a substrate, typically by an ion beam) to a TEM grid in a TEM sample holder 761 for analysis. Stage 724 can also include mounted thereon a flip stage (not shown) as described for example in U.S. Pat. Pub. No. 20040144924 of Asselbergs et al. for "Method for the Manufacture and Transmissive Irradiation of a Sample, and Particle-optical System," which is owned by the applicant of the present invention and which is hereby incorporated by reference. Mounting the TEM grid on the flip stage allows the orientation of the TEM grid to be changed and, with rotation of the stage, allows the sample can be mounted in a desired orientation.

System controller 738 controls the operations of the various parts of dual beam system 702. Through system controller 738, a user can cause ion beam 752 or electron beam 716 to be scanned in a desired manner through commands entered into a conventional user interface (not shown). Alternatively, system controller 738 may control dual beam system 702 in accordance with programmed instructions. FIG. 7 is a schematic representation, which does not include all the elements of a typical dual beam system and which does not reflect the actual appearance and size of, or the relationship between, all the elements.

Although the present invention and its advantages have been described in detail, it should be understood that various changes, substitutions and alterations can be made herein without departing from the spirit and scope of the invention as defined by the appended claims. For example, the use of overlayed differential images of TEM samples can be used in the field of tomography, which includes automated diffraction tomography. This method is known from "Towards automated diffraction tomography: Part I-Data acquisition", U. Kolb et al., Ultramicroscopy 107 (2007) 507-513. The teachings of the embodiments of the current invention can be applied to many different arts, including the use of studying bio samples. It can also be used in the field of cryo-tomography, wherein a system can be provided to look for regions of interest from site A and use the findings to teach a system to find the regions of interest in site B. Tomography can be used to stop milling sequences after the region of interest is removed from a sample site. The invention can also be applied to IR CE applications and subsurface imaging.

I claim:

1. A method for performing endpointing on a sample with a charged particle beam system comprising:
   loading a sample into a charged particle beam system, the charged particle beam system including an ion beam and electron microscope;
   milling, using the ion beam, the sample to expose a first surface of the sample;
   forming, using the electron microscope, a first image of the first surface of the sample;
   milling, using the ion beam, the first surface of the sample to expose a second surface of the sample;
   forming, using the electron microscope, a second image of the second surface of the sample;
   forming a third image by subtracting the first image from the second image, the third image showing the difference made from the ion beam milling to create the second surface; and
   forming a fourth image by overlaying the second image over the first image, the fourth image being a differential image formed by subtracting the second image from the first image, the fourth image showing the difference made from the ion beam milling to create the second surface.

2. The method in accordance with claim 1 wherein the third image or the fourth image can be displayed periodically in a flashing overlay over the first image thereby creating highlights showing where the ion beam last milled.

3. The method in accordance with claim 2 further including:
   milling, using the ion beam, the second surface of the sample to create a third surface of the sample;
   imaging the third surface of the sample using the electron microscope thereby creating a subsequent image of the sample; and
   overlaying the subsequent image over the first image creating a differential image that shows the difference made from the charged particle beam to create the third surface.

4. The method in accordance with claim 2 wherein a controller is used to automate the image collection of the first and second image and the creation of the third differential image, the controller including a computer processor and a computer-readable memory.

5. The method in accordance with claim 4 wherein said controller uses the third differential image as an input to automatically mill the second surface with the ion beam based on the differences from the differential image.

6. The method in accordance with claim 5 wherein a dwell point of the ion beam on a surface of the sample can be determined by the controller using the third differential image.

7. The method in accordance with claim 1 further comprising performing calculations to create a differential image substantially in real time feedback so that an operator of the charged particle beam system can mill a sample with the ion beam immediately following the creation of the differential image.

8. A method for performing endpointing on a sample with a charged particle beam system comprising:
   loading a sample into a charged particle beam system, the charged particle beam system including an ion beam and electron microscope;
   milling, using the ion beam, the sample to expose a first surface of the sample;
   forming, using the electron microscope, a first image of the first surface of the sample;
   milling, using the ion beam, the first surface of the sample to expose a second surface of the sample;
   forming, using the electron microscope, a second image of the second surface of the sample;
   forming a third image by subtracting the second image from the first image, the third image showing the difference made from the ion beam milling to create the second surface; and
   forming a fourth image by overlaying the first image over the second image, the fourth image being a differential image formed by subtracting the first image from the second image, the fourth image showing the difference made from the ion beam milling to create the second surface.

9. The method in accordance with claim 8 where the third image can be displayed periodically in a flashing overlay over the first image thereby creating highlights showing where the ion beam last milled.

10. The method in accordance with claim 8 further including:
   milling, using the ion beam, the second surface of the sample to create a third surface of the sample;
   imaging the third surface of the sample using the electron microscope thereby creating a subsequent image of the sample; and
   overlaying the subsequent image over the first image creating a differential image that shows the difference made from the charged particle beam to create the third surface.

11. The method in accordance with claim 8 wherein a controller is used to automate the image collection of the first and second image and the creation of the third differential image, the controller including a computer processor and a computer-readable memory.

12. The method in accordance with claim 11 wherein said controller uses the third differential image as an input to automatically mill the second surface based on the differences from the differential image.

13. The method in accordance with claim 12 wherein a dwell point of the ion beam on a surface of the sample can be determined by the controller using the third differential image.

14. The method in accordance with claim 9 further comprising performing calculations to create a differential image substantially in real time feedback so that an operator of the charged particle beam system can mill a sample with the ion beam immediately following the creation of the differential image.

* * * * *